United States Patent [19]

Lalinde et al.

[11] Patent Number: 4,939,161

[45] Date of Patent: Jul. 3, 1990

[54] ANALGESIC N-ARYL-N-[1-SUBSTITUTED-3,5-DIMETHYL-4-PIPERIDINYL]AMIDES

[75] Inventors: Nhora L. Lalinde, West Nyack; John Moliterni, Staten Island, both of N.Y.; H. Kenneth Spencer, Chatham, N.J.

[73] Assignee: BOC, Inc., New Providence, N.J.

[21] Appl. No.: 351,677

[22] Filed: May 12, 1989

[51] Int. Cl.$^5$ .................. A61K 31/445; C07D 401/06
[52] U.S. Cl. ...................................... 514/326; 546/211
[58] Field of Search ........................ 546/211; 514/326

[56] References Cited

U.S. PATENT DOCUMENTS

| 3,164,600 | 1/1965 | Janssen | 546/213 |
| 3,998,834 | 12/1976 | Janssen et al. | 546/213 |
| 4,584,303 | 4/1986 | Huang et al. | 514/326 |
| 4,791,121 | 12/1988 | Kudzma et al. | 546/209 X |

OTHER PUBLICATIONS

C. R. Ganellin et al., *J. Med. Chem.*, vol. 8, (1965), pp. 619–625.
G. Stork et al., *J. Amer. Chem. Soc.*, vol. 68, (1946), pp. 1053–1057.
N. J. Harper et al., *J. Med. Chem.*, vol. 7, (1964), pp. 726–728.
Curwain et al., *J. Med. Chem.*, vol. 14, (1971), pp. 737–741.
C. Mannich et al., *Berichte*, vol. 69, (1936), pp. 2299–2305.
V. V. Kuznetsov et al., *Khim. Geterotsikl Soedin*, vol. 7, (1987), pp. 949–953—Index Chemicus Abstract supplied (vol. 108, Issue 1255, Abtr. 409914 (1988)).
B. Huegi et al., *Eur. J. Med. Chem. Chim. Ther.*, vol. 19, (1984), pp. 487–494.
A. H. Becket et al., *J. Med. Pharm. Chem.*, vol. 1, (1959), pp. 37–58.

Primary Examiner—Richard A. Schwartz
Attorney, Agent, or Firm—R. Hain Swope; Larry R. Cassett

[57] ABSTRACT

This invention pertains to novel substituted N-aryl-N-[1-substituted 3,5-dimethyl-4-piperidinyl]amides useful as analgesics, and methods of administering analgesia, which comprises the systemic administration to mammals of such compounds, and pharmaceutical compositions containing such compounds, wherein the novel compounds have the general formula:

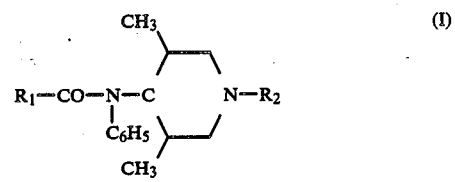

including optically active isomeric forms, cis/trans isomeric forms and the pharmaceutically acceptable acid addition salts thereof, wherein:

$R_1$ is an alkyl group selected from the group consisting of lower-alkyl, and lower-alkoxy lower-alkyl, each alkyl group having from 1 to 6 carbon atoms; and $R_2$ is a member selected from the group consisting of phenyl lower-alkyl, pyridinyl, lower-alkyl, thienyl lower-alkyl, pyrazolyl lower-alkyl, tetrazolyl lower-alkyl, 4,5-dihydro-5-oxo-1H-tetrazolyl lower-alkyl, 1,3-dihydro-1,3-dioxo-2H-isoindolyl (N-phthalimidyl) lower-alkyl, and 2,3-dihydro-2-oxo-1H-benzimidazolyl lower-alkyl.

15 Claims, No Drawings

ANALGESIC N-ARYL-N-[1-SUBSTITUTED-3,5-DIMETHYL-4-PIPERIDINYL]AMIDES

The present invention relates to N-aryl-N-[1-substituted 3,5-dimethyl-4-piperidinyl]amides and pharmaceutical compositions and methods employing such compounds. In particular, this new class of compounds possesses potent analgesic and anesthetic properties.

BACKGROUND OF THE INVENTION

A number of patents disclose certain N-aryl-N-(1-substituted-4-piperidinyl)amides having analgesic activity. For example, U.S. Pat. No. 3,998,834 and 3,164,600, issued to Janssen et al. and assigned to Janssen Pharmaceuticals N. V., disclose certain N-phenyl-N-[N-(aryl-substituted)-4-piperidinyl]-amide compounds and N-aryl-N-[N-(arylalkyl)-4-piperidinyl]amines, respectively, useful as analgesics. U.S. Pat. No. 4,584,303, issued to Huang et al. and assigned to The BOC Group, Inc., discloses certain N-phenyl-N-[N-(heterocyclic)-4-piperidinyl]amide compounds useful as analgesics.

C. R. Ganellin et al., *J. Med. Chem.*, 8, pp. 619–625 (1965) disclose the preparation of N-arylalkyl-3-methyl-4-piperidone derivatives. G. Stork et al., *J. Amer. Chem Soc.*, 68, pp. 1053–1057 (1946) disclose the preparation of N-benzoyl-3-ethyl-3-carboethoxy-4-piperidone derivatives. N. J. Harper et al., *J. Med. Chem.*, 7, pp. 726–728 (1964) disclose the preparation of certain 1-substituted-3,5-dimethyl-4-piperidinols which have no activity compared to the 1, 2, 5 and 1, 2, 3-trimethyl substituted piperidinols. Curwain et al., *J. Med. Chem.*, 7 pp.737–741 (1964) disclose the preparation of certain N-(guanidinoalkyl)pyrrolidine derivatives. C. Mannich et al., *Beilstein.* 69. pp. 2299–2305 (1936), discloses generally substituted-3,5-dialkyl-4-piperidone derivatives. V. V. Kuznetsov et al., *Khim. Geterotsikl Soedin*, 7, pp. 949–953 (1987), disclose 1-substituted 4-(N-aryl(alkyl)amino)-2,5-dimethyl-piperidines and their N-acyl derivatives having analgesic activity.

SUMMARY OF THE INVENTION

This invention pertains to novel substituted N-aryl-N-[1-substituted 3,5-dimethyl-4-piperidinyl]amides useful as analgesics, and methods of administering analgesia, which comprises the systemic administration to mammals of such compounds, and pharmaceutical compositions containing such compounds, wherein the novel compounds have the general formula:

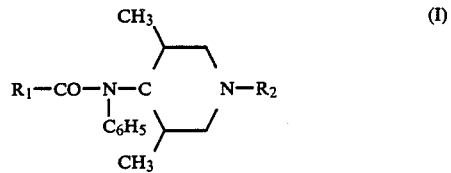

including optically active isomeric forms, cis/trans isomeric forms and the pharmaceutically acceptable acid addition salts thereof, wherein:

$R_1$ is an alkyl group selected from the group consisting of lower-alkyl, and lower-alkoxy lower-alkyl, each alkyl group having from 1 to 6 carbon atoms; and $R_2$ is a member selected from the group consisting of phenyl lower-alkyl, pyridinyl lower-alkyl, thienyl lower-alkyl, pyrazolyl lower-alkyl, tetrazolyl lower-alkyl, 4,5-dihydro-5-oxo-1H-tetrazolyl lower-alkyl, 1,3-dihydro-1,3-dioxo-2H-isoindolyl (N-phthalimidyl) lower-alkyl, and 2,3-dihydro-2-oxo-1H-benzimidazolyl lower-alkyl.

DETAILED DESCRIPTION OF THE INVENTION

The compounds of the present invention possess very desirable analgesic activities. In particular, the inventive compounds have central nervous system depressant properties which include analgesia, hypnosis, sedation, muscle relaxation, increased pain threshold, and barbiturate and/or general anesthetic potentiation. Many of the compounds provide highly potent analgesia with immediate onset and a short duration of action. These properties are highly desirable in circumstances where acute severe pain must be eliminated over a short period of time, such as in anesthesiology. The preferred compounds of the present invention have been found to provide reduced rigidity at high doses, superior motor coordination recovery, or less respiratory and/or cardiovascular depressive activity when compared to fentanyl, N-phenyl-N-[1-(2-phenylethyl)-4-piperidinyl]-propanamide.

The compounds of the present invention may be used together with a pharmaceutically acceptable carrier to provide pharmaceutical compositions and can be administered to mammals such as man in amounts sufficient to provide analgesic effects.

As set out above, the analgesic compounds of the present invention have the general formula (I):

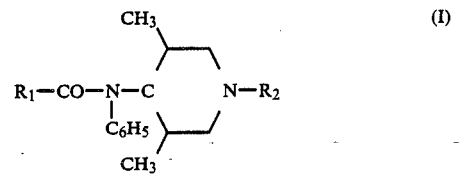

including optically active isomeric forms, cis/trans isomeric forms and the pharmaceutically acceptable acid addition salts thereof, wherein $R_1$ and $R_2$ are defined as set forth below.

Group $R_1$ in Formula (I) above is an alkyl group selected from the group consisting of lower-alkyl, and lower-alkoxy lower-alkyl, each alkyl group having from 1 to 6 carbon atoms. Suitable $R_1$ groups include methyl, ethyl, propyl, butyl, pentyl, hexyl, methoxymethyl, ethoxymethyl, 1-propoxymethyl, 2-propoxymethyl, 1-butoxymethyl, 1-pentoxymethyl, 1-hexoxymethyl, 1-methoxyethyl, 1-ethoxy-1-ethyl, and 1-butoxy-1-ethyl. In a preferred embodiment, the $R_1$ group is a member selected from the group consisting of methyl, ethyl, methoxymethyl and 1-methoxyethyl.

Group $R_2$ in Formula I above is a substituted or unsubstituted ring system selected from the group consisting of phenyl lower-alkyl, monocyclic heterocyclic lower-alkyl ring systems having 5 to 6 ring member atoms and fused bicyclic and tricyclic heterocyclic lower-alkyl ring systems having 5 to 6 ring member atoms in each ring of the polycyclic ring system. The heteroatom may be selected from the group consisting of nitrogen, sulfur and oxygen.

In a preferred embodiment, group $R_2$ in Formula (I) above is a member selected from the group consisting of phenyl lower-alkyl, pyridinyl lower-alkyl, thienyl lower-alkyl, pyrazolyl lower-alkyl, tetrazolyl lower-alkyl, 4,5-dihydro-5-oxo-1H-tetrazolyl lower-alkyl, 1,3-dihydro-1,3-dioxo-2H-isoindolyl (N-phthalimidyl) lower-alkyl, and 2,3-dihydro-2-oxo-1H-benzimidazolyl lower-alkyl.

In a more preferred embodiment, group $R_2$ in Formula (I) above is a member selected from the group consisting of phenyl lower-alkyl, 2-pyridinyl lower-alkyl, 3-pyridinyl lower-alkyl, 2-thienyl lower-alkyl, 3-thienyl lower-alkyl, 1H-pyrazol-1-yl lower-alkyl, 2H-tetrazol-2-yl lower-alkyl, 4,5-dihydro-5-oxo-1H-tetrazol-1-yl lower-alkyl which is substituted in the 4-position with lower-alkyl, 1,3-dihydro-1,3-dioxo-2H-isoindol-2-yl (N-phthalimidyl) lower-alkyl, and 2,3-dihydro-2-oxo-1H-benzimidazolyl lower-alkyl which is substituted in the 3-position with lower-alkyl.

In a most preferred embodiment, group $R_2$ in Formula (I) above is a member selected from the group consisting of phenylmethyl, 2-phenylethyl, 2-(2-pyridinyl)ethyl, 2-(2-thienyl)ethyl, 2-(1H-pyrazol-1-yl)ethyl, 2-(2H-tetrazol-2-yl)ethyl, 2-(4-ethyl-4,5-dihydro-5-oxo-1H-tetrazol-1-yl)ethyl, 2-(1,3-dihydro-1,3-dioxo-2H-isoindol-2-yl)ethyl, and 2-(3-ethyl-2,3-dihydro-2-oxo-1H-benzimidazol-1-yl)ethyl2-(dihydro-oxobenzimidazolyl)ethyl.

The phenyl or heterocyclic ring may be unsubstituted or substituted, wherein the substituent group is a member independently selected from the group consisting of halogen, lower-alkyl, lower-alkoxy, halogenated lower-alkyl, and combinations thereof. In a preferred embodiment, the substituent group is a member selected from the group consisting of fluoro, chloro, iodo, methyl, ethyl, isopropyl, methoxy, trifluoromethyl, and combinations thereof.

The lower-alkyl group is a member selected from the group consisting of branched or unbranched hydrocarbon groups containing from 1 to 7 carbon atoms. In a preferred embodiment, the lower-alkyl group is a member selected from the group consisting of methyl and ethyl.

The term lower-alkyl groups, as used herein, means branched or unbranched hydrocarbon groups containing from 1 to 7 carbon atoms. The term lower-alkoxy groups, as used herein, means branched or unbranched hydrocarboxy groups containing from 1 to 7 carbon atoms. Preferred heterocyclic groups include from 2 to 12 member atoms and can include the substituents discussed above in connection with heterocyclic groups. The term halogen, as used herein, refers to the chemically related elements consisting of fluorine, chlorine, bromine and iodine.

The compounds of the present invention which have at least one asymmetric carbon atom can exist in optically active isomeric forms. For example, in compounds in which $R_2$ is a 2-phenyl-1-propyl or 1-phenyl-2-propyl group, etc., the carbon adjacent to the piperidinyl nitrogen is an asymmetric carbon atom and such compounds can therefore exist in optical active isomeric (enantiomeric) forms. Such isomeric forms can be isolated from the racemic mixtures by techniques known to those skilled in the art.

The 3,5-dimethyl substituted compounds of the present invention exist in cis and trans form. Such compounds can be used as a mixture of such forms but many times one form is more active than the other or one form has other desirable characteristics. Thus many times it is desirable to resolve the cis/trans mixture. This resolution can be accomplished by techniques conventional in the art for such purpose, e.g., chromatographic techniques such as column chromatography or high pressure liquid chromatography or simple recrystallization techniques.

The compounds of the present invention can be prepared by various methods. In one example of a method for preparing the compounds of the present invention, the compounds are prepared according to reaction Scheme 1 illustrated below (See generally Huegi et al., Eur. J. Med. Chem. Chim Ther., 19, pp. 487–494 (1984) and A. W. Beckett et al., J. Med. Pharm. Chem. 1, pp. 37–58 (1959)).

Benzylamine 1 is sequentially alkylated, first with methyl methacrylate, then with ethyl acrylate to give tertiary amine intermediate 2. Intermediate 2 is then condensed under alkaline conditions to cyclic intermediate 3. Intermediate 3 is reacted with aniline to form the Schiff base which is then reduced with, for example, sodium cyanoborohydride to yield the corresponding amine 4. Intermediate 4 is then reduced with, for example, lithium aluminum hydride to provide the alcohol intermediate 5. Intermediate 5 is reacted with methanesulfonyl chloride to yield the mesyl derivative 6 which is then reduced to the 3,5-dimethyl intermediate 7. Intermediate 7 is acylated with an appropriate acid halide, e.g. $R_1COCl$, or an anhydride, e.g. $(R_1 CO)O$, to introduce the desired $R_1$-carbonyl group on the nitrogen atom and thereby obtain compound 8 having formula (I) of the present invention.

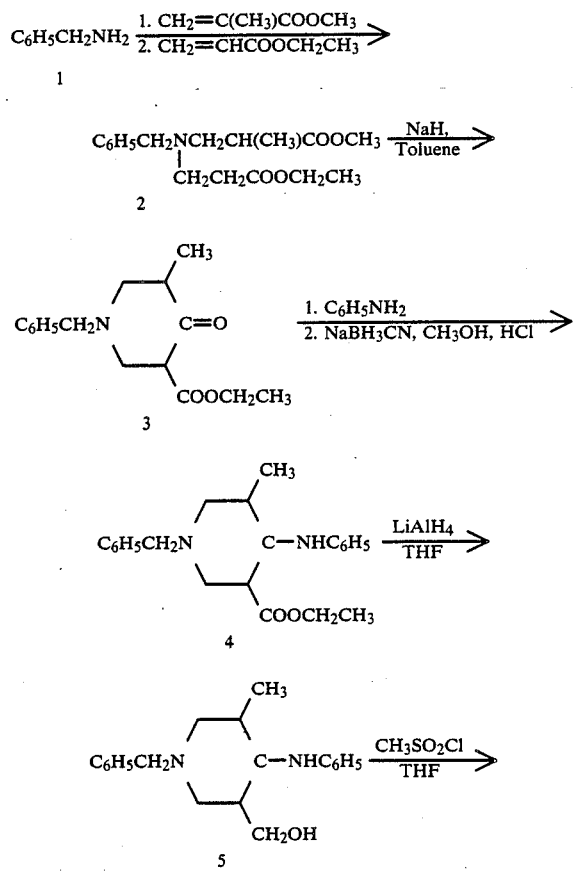

SCHEME 1

-continued
SCHEME 1

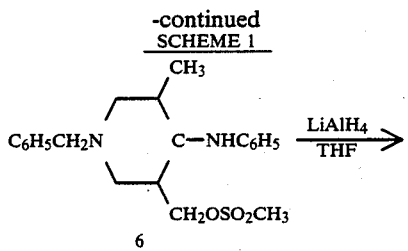

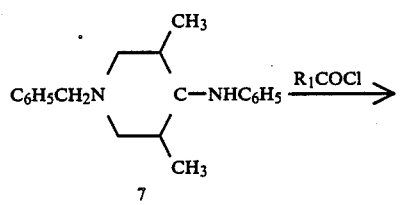

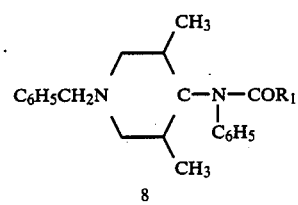

When the desired $R_2$ group is not phenylmethyl, one procedure for preparing compounds of the present invention with different $R_2$ groups is to remove the phenylmethyl group in compound 8 by hydrogenolysis (e.g., $H_2$, $Pd(OH)_2$). The desired $R_2$ substituent group can then be introduced by reacting compound 9 with an appropriately reactive molecule $R_2$-X, wherein X is halogen, such as chlorine, bromine or iodine, or its reactive equivalent, to obtain compound 10 having formula (I) according to reaction Scheme 2 illustrated below.

SCHEME 2

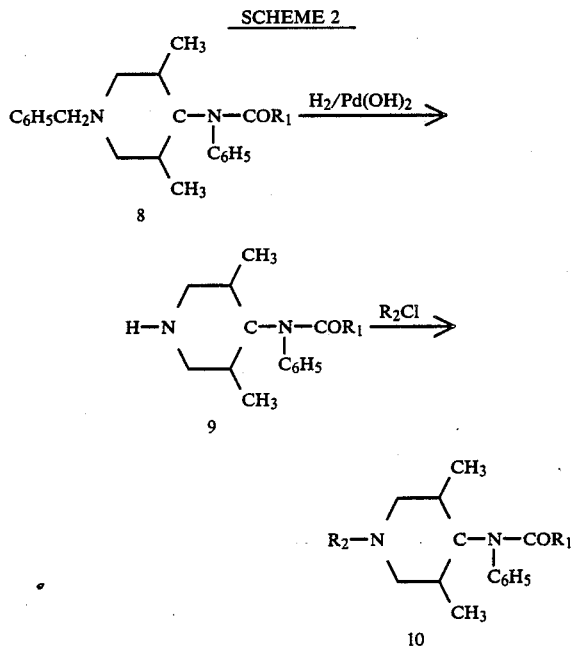

The cis and trans isomers of the compounds of the present invention can be separated at various stages in the reaction scheme by conventional means and are conveniently separated after reduction of the ester group to form compound 5.

The compounds of the present invention while effective in the form of the free base may be formulated and administered in the form of the therapeutically or pharmaceutically acceptable acid addition salts for purposes of stability, convenience of crystallization, increased solubility and the like. These acid addition salts include inorganic acid salts such as hydrochloric, hydrobromic, sulfuric, nitric, phosphoric, perchloric acid salts and the like; and organic acid salts such as acetic, trifluoroacetic, propionic, oxalic, hydroxyacetic, methoxyacetic, 2-hydroxypropanoic, 2-oxopropanoic, propanedioic, 2-hydroxy-butanedioic, benzoic, 2-hydroxybenzoic, 4 amino-2-hydroxy-benzoic, 3-phenyl-2-propenoic, alpha-hydroxybenzeneacetic, methanesulfonic, ethanesulfonic, benzenesulfonic, toluene-sulfonic, cyclohexanesulfamic, succinic, tartaric, citric, maleic, fumaric acid salts and the like. The preferred acid addition salts are chloride, oxalate and citrate. These acid addition salts can be prepared by conventional methods, such as by treatment of the free base of the inventive compound with the appropriate acid.

The compounds of the present invention, prepared in the free base form, can be combined with a pharmaceutically acceptable carrier to provide a pharmaceutical composition. Suitable carriers for the free bases include propylene glycol-alcohol-water, isotonic water, sterile water for injection (USP), emulphor TM -alcohol water, cremophor-EL TM or other suitable carriers known to those skilled in the art.

The compounds of the present invention, prepared in the pharmaceutically acceptable acid addition salt form, can also be combined with a pharmaceutically acceptable carrier to provide a pharmaceutical composition. Suitable carriers for the acid addition salts include isotonic water, sterile water for injection (USP), alone or in combination with other solubilizing agents such as ethanol, propylene glycol, or other conventional solubilizing agents known to those skilled in the art.

Of course, the type of carrier will vary depending upon the mode of administration desired for the pharmaceutical composition as is conventional in the art. A preferred carrier is an isotonic aqueous solution of the inventive compound.

The compounds of the present invention can be administered to mammals, e.g., animals or humans, in amounts effective to provide the desired analgesic therapeutic effect or to reverse the actions of an opiate analgesic. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can be as low as about 0.00005 mg/kg, which the practitioner may titrate to the desired effect.

The compounds of the present invention can be administered parenterally, in the form of sterile solutions or suspensions, such as intravenously, intramuscularly or subcutaneously in the carriers previously described. The compounds may also be administered orally, in the form of pills, tablets, capsules, troches, and the like, as well as sublingually, rectally, or transcutaneously with a suitable pharmaceutically acceptable carrier for that particular mode of administration as is conventional in the art.

For parenteral therapeutic administration, the compounds of the present invention may be incorporated into a sterile solution or suspension. These preparations should contain at least about 0.1% of the inventive compound, by weight, but this amount may be varied to between about 0.1% and about 50% of the inventive compound, by weight of the parenteral composition. The exact amount of the inventive compound present in such compositions is such that a suitable dosage level will be obtained. Preferred compositions and preparations according to the present invention are prepared so that a paranteral dosage unit contains from between about 0.5 to about 100 milligrams of the inventive compound.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parenteral preparations may be enclosed in ampules, disposable syringes, or multiple dose vials made of glass or plastic.

The compounds of the present invention can also be administered orally. For oral therapeutic administration, the compounds may be incorporated with excipients and used in the form of tablets, capsules, elixirs, suspensions, syrups, wafers, chewing gums and the like. These preparations should contain at least about 4% of the inventive compound, by weight, but this amount may be varied depending upon the particular dosage form from between about 4% to about 70% of the inventive compound, by weight of the oral composition. The exact amount of the compound present in the composition is such that a suitable dosage will be obtained. Preferred compositions and preparations according to the present invention are prepared so that an oral dosage unit form contains from between about 5 to about 300 milligrams of the inventive compound.

The tablets, pills, capsules, troches and the like may also contain the following adjuvants: a binder, such as microcrystalline cellulose, gum tragacanth or gelatine; an excipient, such as starch or lactose; a disintegrating agent, such as alginic acid, Primogel, corn starch and the like; a lubricating agent, such as magnesium stearate or Sterotex; a gliding agent, such as colloidal silicon dioxide; a sweetening agent, such as sucrose or saccharin; and a flavoring agent, such as peppermint, methyl salicylate or orange flavoring. When the dosage form is a capsule, it may additionally contain a liquid carrier such as a fatty oil. Other dosage unit forms may contain other materials which modify the physical form of the dosage unit, such as enteric coatings. Thus tablets or pills may be coated with sugar, shellac, or other enteric coating agents. A syrup may contain, in addition to the above adjuvants, sucrose as a sweetening agent, preservatives, dyes, coloring agents and flavoring agents.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is further illustrated by the following examples which are presented for purposes of demonstrating, but not limiting, the preparation of the compounds and compositions of this invention. Related methods for preparing compounds of the type of the present invention are disclosed in U.S. Pat. No. 4,584,303, which disclosure is incorporated herein by reference.

EXAMPLE 1

This Example illustrates the preparation of 3-phenylmethylamino-2-methyl-propanoic acid methyl ester.

Methyl methacrylate (64.2 ml, 60.07 g, 0.6 mole) was added slowly at 0° C. (ice bath) to benzylamine (54.6 ml, 53.6 g, 0.5 mole) in 200 ml of methanol. The reaction solution was heated to reflux overnight. After being cooled, the solution was concentrated under vacuum to remove the excess of methyl methacrylate and methanol. Unreacted benzylamine was removed by heating the residue in a Kugelrohr oven under vacuum to yield the crude 3-phenylmethylamino-2-methyl-propanoic acid methyl ester (79.2 g, 76.41%).

EXAMPLE 2

This Example illustrates the preparation of N-[2-(methoxycarbonyl)propyl]-N-[2-(ethoxycarbonyl)ethyl]-phenylmethylamine.

3-Phenylmethylamino-2-methyl-propanoic acid methyl ester (79 g, 0.38 mole) from Example and ethyl acrylate (54.2 ml, 50.06 g, 0.5 mole) were dissolved in 200 ml of methanol and then heated to reflux overnight. After being cooled, the solution was concentrated under vacuum to remove the excess of solvent and ethyl acrylate to yield the crude N-[2-(methoxycarbonyl)propyl]-N-[2-(ethoxycarbonyl)ethyl]phenylmethylamine (110 g, 95%).

EXAMPLE 3

This Example illustrates the preparation of 1-phenylmethyl-3-methyl-5-methoxycarbonyl-4-piperidone.

N-[2-(Methoxycarbonyl)propyl]-N-[2-(ethoxycarbonyl)ethyl]phenylmethylamine (120.36g, 0.4 mole) from Example 2 in toluene (50 ml) was added slowly to a solution of 12 g (0.4 mole, 80% oil suspension) of sodium hydride in 300 ml of toluene. After the addition was complete, the temperature of the reaction solution was raised to 90° C. and maintained at this temperature overnight. After being cooled, the reaction solution was quenched with 200 ml of water, then extracted with ether to yield 98.54 g (70%) of the crude 1-phenylmethyl-3-methyl-5-methoxycarbonyl-4-piperidone.

EXAMPLE 4

This Example illustrates the preparation of 1-phenylmethyl-3-methyl-5-methoxycarbonyl-4-(N-phenylamino)piperidine.

Sodium cyanoborohydride (0.69 g, 11 mmole) and 26 g of 30A molecular sieves were slowly added at room temperature to a stirred solution of 1-phenylmethyl-3-methyl-5-methoxycarbonyl-4-piperidone (5.04 g, 18.3 mmole) from Example 3 in 200 ml of methanol, 10.22 g (110 mmole) of aniline and 9.48 ml of 3.86N hydrochloric acid (36.6 mmole) in methanol. The reaction mixture was stirred at room temperature for 3 days, after which time the molecular sieves were filtered off and the solution was made acidic with 10 ml of 20% hydrochloric acid. The methanol was evaporated under vacuum and the residue was diluted with 100 ml of water then extracted with ether. The aqueous layer was then made alkaline with dilute aqueous sodium hydroxide and extracted with 3×100 ml of ether. The combined organic layers were concentrated under vacuum to yield 3.87 g (60%) of crude 1-phenylmethyl-3-methyl-5-methoxycarbonyl-4-(N-phenylamino)piperidine.

EXAMPLE 5

This Example illustrates the preparation of 1-phenylmethyl-3-methyl-5-methanol-4-(N-phenylamino)piperidine.

1-Phenylmethyl-3-methyl-5-methoxycarbonyl-4-(N-phenylamino)piperidine (2.3 g, 6.5 mmole) from Example 4 in 30 ml of tetrahydrofuran was slowly added to a suspension of lithium aluminum hydride (1.24 g, 32.6 mmole) in 20 ml of dry tetrahydrofuran. After being stirred at room temperature for 1.5 hours, the reaction mixture was quenched by the slow addition of 10 ml of saturated magnesium sulfate solution. The reaction mixture was then diluted with 100 ml of water, the organic layer was decanted, the solids rinsed with tetrahydrofuran, and the combined organic layers were dried. Thin layer chromatography analysis of the solution revealed two isomers: The major isomer, A, had an Rf of 0.29; The minor isomer, B, had an Rf of 0.19. The isomers were separated on a chromatography column (silica gel; eluted with ethyl acetate/hexane; 1:2) to yield 0.45 g (22.3 %) of isomer A and 0.21 g (10.4 %) of isomer B of 1-phenylmethyl-3-methyl-5-methanol-4-(N-phenylamino)piperidine.

EXAMPLE 6

This Example illustrates the preparation of 1-phenylmethyl-3-methyl-5-(methylene-0-mesyl)-4-(N-phenylamino)piperidine.

Triethylamine (0.39 g, 3.86 mmole) and methanesulfonyl chloride (0.41 g, 3.54 mmole) in 10 ml of dichloromethane were added to 1-phenylmethyl-3-methyl-5-methanol-4-(N-phenylamino)piperidine (1 g, 3.22 mmole) from Example 5 in 10 ml of dichloromethane. The reaction mixture was stirred at room temperature over a period of 45 minutes. After concentration of the reaction mixture under vacuum, thin layer chromatography of the crude residue of 1-phenylmethyl-3-methyl-5-(methylene-O-mesyl)-4-(N-phenyl-amino)piperidine showed complete reaction (1,25 g, 91% yield).

EXAMPLE 7

This Example illustrates the preparation of 1-phenylmethyl-3,5-dimethyl-4-(N-phenylamino)piperidine.

A solution of 1-phenylmethyl-3-methyl-5-(methylene-0-mesyl)-4-(N-phenyl-amino)piperidine (1.02 g, 2.6 mmole) from Example 6 in 10 ml of tetrahydrofuran was added slowly to a suspension of lithium aluminum hydride (0.5 g, 13.1 mmole) in 20 ml of dry tetrahydrofuran. The reaction mixture was heated to reflux and maintained at this temperature overnight. After being cooled, the reaction mixture was quenched by the addition of 10 ml of saturated sodium sulfate solution, whereupon the organic layer separated. The inorganic salts were rinsed with tetrahydrofuran, the organic layers combined, then dried and concentrated under vacuum. The product residue was purified by chromatography (silica gel; ethyl acetate/hexane; 1:4) to yield 0.69 gg (90%) of 1-phenylmethyl-3,5-dimethyl-4-(N-phenylamino)piperidine.

EXAMPLE 8

This Example illustrates the preparation of N-(phenyl)-N-(1-phenylmethyl-3,5-dimethyl-4-piperidinyl)]propanamide.

Propionyl chloride (6.9 g, 75 mmole) was added to 1-phenylmethyl-3,5-dimethyl-4-(N-phenylamino)piperidine (4.4 g, 15 mmole) from Example 7 in 100 ml of dichloromethane. The reaction solution was stirred at room temperature overnight and subsequently diluted with 20 ml of 10% sodium hydroxide solution. The organic layer was separated and the aqueous layer was extracted with 2 ×40 ml of dichloromethane. The combined organic layers were dried and concentrated under vacuum. The crude residue was purified by chromatography (silica gel; ethyl acetate/hexane; 1:2.5) to yield 5 g 60 %) of pure N-(phenyl)-N-(1-phenylmethyl-3,5-dimethyl-4-piperidinyl)]-propanamide.

EXAMPLE 9

This Example illustrates the preparation of 3,5-dimethyl-4-(N-phenyl-(propanamidyl))piperidine.

N-(Phenyl)-N-(1-phenylmethyl-3,5-dimethyl-4-piperidinyl)]-propanamide (5 g, 14 mmole) from Example 8 was hydrogenated in 200 ml of ethanol using 500 mg of Pd(OH) as catalyst. After the usual work-up, 3 g (82.4 %) of 3,5-dimethyl-4-(N-phenyl-(propanamidyl))piperidine was obtained.

EXAMPLE 10

This Example illustrates the preparation of N-(phenyl)-N-[1-(2-(1,3-dihydro-1,3-dioxo-2H-isoindol-2-yl)ethyl)-3,5-dimethyl-4-piperidinyl]propanamide.

3,5-Dimethyl-4-(N-phenyl-(propanamidyl))piperidine (0.428 g, 1.64 mmole) from Example 9, n-(2bromoethylphthalimide) (0.46 g, 1.8 mmole) and 1.13 g of potassium carbonate in 50 ml of acetonitrile were heated to reflux overnight. The reaction solution was concentrated under vacuum and the crude residue was purified by chromatography (silica gel; ethyl acetate/hexane; 1.5:2 to yield 0.43 g (60 %) of pure N-(phenyl)-N-[1-(2-(1,3-dihydro-1,3-dioxo-2H-isoindol-2-y)ethyl)-3,5-dimethyl-4-piperidinyl]propanamide; the oxalate salt of which had m.p. 127°–129° C.

EXAMPLES 11–32

Further examples of compounds within the scope of the present invention which may be prepared by procedures analogous to those described above include:

N-(phenyl)-N-[1-(2-(2-pyridinyl)ethyl)-3,5-dimethyl-4-piperidinyl]methoxyacetamide (minor isomer)

N-(phenyl)-N-[1-(2-(4-ethyl-4,5-dihydro-5-oxo-1H-tetrazol-1-yl)ethyl)-3,5-dimethyl-4piperidinyl]-methoxyacetamide N-(phenyl)-N-[1-(2-(phenyl)ethyl)-3,5-dimethyl-4-piperidinyl]methoxyacetamide (major isomer)

N-(phenyl)-N-[1-(2-(2H-tetrazol-2-yl)ethyl)-3,5-dimethyl-4-piperidinyl]methoxyacetamide N-(phenyl)-N-[1-(2-(1H-pyrazol-1-yl)ethyl)-3,5-dimethyl-4-piperidinyl]methoxyacetamide N-(phenyl)-N-[1-(phenylmethyl)-3,5-dimethyl-4-piperidinyl]methoxyacetamide (major isomer)

N-(phenyl)-N-[1-(2-(1,3-dihydro-1,3-dioxo-2H-isoindol-2-yl)ethyl)-3,5-dimethyl-4-piperidinyl]methoxyacetamide N-(phenyl)-N-[1-(phenylmethyl)-3,5-dimethyl-4-piperidinyl]methoxyacetamide (minor isomer)

N-(phenyl)-N-[1-(2-(2-pyridinyl)ethyl)-3,5-dimethyl-4-piperidinyl]methoxyacetamide (minor isomer)

N-(phenyl)-N-[1-(2-(phenyl)ethyl)-3,5-dimethyl-4-piperidinyl]methoxyacetamide (minor isomer)

N-(phenyl)-N-[1-(2-(1,3-dihydro-1,3-dioxo-2H-isoindol-2-yl)ethyl)-3,5-dimethyl-4-piperidinyl]-propanamide (major isomer)

N-(phenyl)-N-[1-(2-(1H-pyrazol-1-yl)ethyl)-3,5-dimethyl-4-piperidinyl]propanamide (major isomer)

N-(phenyl)-N-[1-(2-(2H-tetrazol-2-yl)ethyl)-3,5-dimethyl-4-piperidinyl]propanamide (major isomer)

N-(phenyl)-N-[1-(phenylmethyl)-3,5-dimethyl-4-piperidinyl]-propanamide (major isomer)

N-(phenyl)-N-[1-(2-(4-ethyl-4,5-dihydro-5-oxo-1H-tetrazol-1-yl)ethyl)-3,5-dimethyl-4-piperidinyl]propanamide (major isomer)

N-(phenyl)-N-[1-(phenylmethyl)-3,5-dimethyl-4piperidinyl]-2-methoxypropanamide (minor isomer)

N-(phenyl)-N-[1-(2-(3-ethyl-2,3-dihydro-2-oxo-1H-benzimidazol-1-yl)ethyl)-3,5-dimethyl-4-piperidinyl]-propanamide (minor isomer)

N-(phenyl)-N-[1-(2-(2H-tetrazol-2-yl)ethyl)-3,5-dimethyl-4-piperidinyl]-propanamide (minor isomer)

N-(phenyl)-N-[1-(2-(1,3-dihydro-1,3-dioxo-2H-isoindol-2-yl)ethyl)-3,5-dimethyl-4-piperidinyl]propanamide (minor isomer)

N-(phenyl)-N-[1-(2-(2-pyridinyl)ethyl)-3,5-dimethyl-4-piperidinyl]propanamide (minor isomer)

N-(phenyl)-N-[1-(2-(1H-pyrazol-1-yl)ethyl)-3,5-dimethyl-4-piperidinyl]propanamide (minor isomer)

N-(phenyl)-N-[1-(2-(4-ethyl-4,5-dihydro-5-oxo-1H-tetrazol-1-yl)ethyl)-3,5-dimethyl-4-piperidinyl]propanamide (minor isomer)

EXAMPLE 33

A pharmaceutical composition for parenteral or intravenous analgesic administration can be prepared from the following ingredients:

| COMPONENTS | AMOUNTS |
|---|---|
| N-(phenyl)-N-[1-(2-(2-pyridinyl)-ethyl)-3,5-dimethyl-4-piperidinyl]methoxyacetamide | 1 mg |
| isotonic water | 10 liters |

Of course, other compounds of this invention such as those set out in Examples 11–32 may be substituted for N-(phenyl)-N-[1-(2-(2-pyridinyl)-ethyl)-3,5-dimethyl-4-piperidinyl]methoxyacetamide with the relative amount of such other compounds in the compositions depending upon their analgesic activity.

EXAMPLE 34

A number of compounds in accordance with the present invention were tested for their analgesic properties. Specifically, the acid addition salts of the compounds, tested in accordance with the invention, were dissolved in sterile water for injection, USP, to form a solution, the concentration of which may vary from 0.00001 mg/ml to 5 mg/ml. The solution was administered intravenously into a mouse tail vain. The ED50 values were obtained from the mouse hot plate analgesia test (58° C.) as described in Domer, Floyd R., Animal Experiments in Pharmacological Analysis, Charles C. Thomas, Springfield, 1971, p. 283 ff. The compounds listed in Table 1 were tested by this procedure and found to have the activities listed in the columns on the right side of Table 1.

TABLE 1

| | COMPOUNDS | M.P. °C. (oxalate salt) | $ED_{50}$ Mg/Kg | Isomer |
|---|---|---|---|---|
| 1. | N-(phenyl)-N-[1-(2-(2-pyridinyl)ethyl)-3,5-dimethyl-4-piperidinyl]methoxyacetamide | 90–93 | 0.025 | A** |
| 2. | N-(phenyl)-N-[1-(2-(4-ethyl-4,5-dihydro-5-oxo-1H-tetrazol-1-yl)ethyl)-3,5-dimethyl-4-piperidinyl]methoxyacetamide | 96–98 | I* | A |
| 3. | N-(phenyl)-N-[1-(2-(phenyl)ethyl)-3,5-dimethyl-4-piperidinyl]methoxyacetamide | 190–191 | 0.143 | A |
| 4. | N-(phenyl)-N-[1-(2-(2H-tetrazol-2-yl)ethyl)-3,5-dimethyl-4-piperidinyl]methoxyacetamide | 101–104 | I | A |
| 5. | N-(phenyl)-N-[1-(2-(1H-pyrazol-1-yl)ethyl)-3,5-dimethyl-4-piperidinyl]methoxyacetamide | 105–107 | 0.0025 | A |
| 6. | N-(phenyl)-N-[1-(phenylmethyl)-3,5-dimethyl-4-piperidinyl]methoxyacetamide | 96–98 | 0.004 | A |
| 7. | N-(phenyl)-N-[1-(2-(1,3-dihydro-1,3-dioxo-2H-isoindol-2-yl)ethyl)-3,5-dimethyl-4-piperidinyl]methoxyacetamide | 121–125 | I | A |
| 8. | N-(phenyl)-N-[1-(phenylmethyl)-3,5-dimethyl-4-piperidinyl]methoxyacetamide | 94–96 | I | B*** |
| 9. | N-(phenyl)-N-[1-(2-(2-pyridinyl)ethyl)-3,5-dimethyl-4-piperidinyl]methoxyacetamide | 130–132 | 0.0035 | B |
| 10. | N-(phenyl)-N-[1-(2-(phenyl)ethyl)-3,5-dimethyl-4-piperidinyl]methoxyacetamide | 135–136 | 0.082 | B |
| 11. | N-(phenyl)-N-[1-(2-(phenyl)ethyl)-3,5-dimethyl-4-piperidinyl]methoxyacetamide | 171–172 | 0.0119 | Mixture |
| 12. | N-(phenyl)-N-[1-(2-(1,3-dihydro-1,3-dioxo-2H-isoindol-2-yl)ethyl)-3,5-dimethyl-4-piperidinyl]propanamide | 127–129 | I | A |
| 13. | N-(phenyl)-N-[1-(2-(1H-pyrazol-1-yl)ethyl)-3,5-dimethyl-4-piperidinyl]propanamide | 171–172 | 0.554I | A |
| 14. | N-(phenyl)-N-[1-(2-(2H-tetrazol-2-yl)ethyl)-3,5-dimethyl-4-piperidinyl]propanamide | 91–93 | 2.00 | A |
| 15. | N-(phenyl)-N-[1-(phenylmethyl)-3,5-dimethyl- | 217–218 | 0.145 | A |

TABLE 1-continued

| | COMPOUNDS | M.P. °C. (oxalate salt) | $ED_{50}$ Mg/Kg | Isomer |
|---|---|---|---|---|
| | 4-piperidinyl]propanamide | | | |
| 16. | N-(phenyl)-N-[1-(2-(1H-pyrazol-1-yl)ethyl)-3,5-dimethyl-4-piperidinyl]propanamide | 119–121 | 0.361 | A |
| 17. | N-(phenyl)-N-[1-(2-(4-ethyl-4,5-dihydro-5-oxo-1H-tetrazol-1-yl)ethyl)-3,5-dimethyl-4-piperidinyl]propanamide | 115–116 | 2.250 | A |
| 18. | N-(phenyl)-N-[1-(phenylmethyl)-3,5-dimethyl-4-piperidinyl]-2-methoxypropanamide | 189–191 | 0.1047 | Mixture |
| 19. | N-(phenyl)-N-[1-(phenylmethyl)-3,5-dimethyl-4-piperidinyl]propanamide | 219–220 | 0.170 | B |
| 20. | N-(phenyl)-N-[1-(2-(3-ethyl-2,3-dihydro-2-oxo-1H-benzimidazol-1-yl)ethyl)-3,5-dimethyl-4-piperidinyl]propanamide | 163–164 | 2.5 | B |
| 21. | N-(phenyl)-N-[1-(2-(2H-tetrazol-2-yl)-ethyl)-3,5-dimethyl-4-piperidinyl]-propanamide | 96–98 | 2.5 | B |
| 22. | N-(phenyl)-N-[1-(2-(1,3-dihydro-1,3-dioxo-2H-isoindol-2-yl)ethyl)-3,5-dimethyl-4-piperidinyl]propanamide | 126–128 | 5.0 | B |
| 23. | N-(phenyl)-N-[1-(2-(2-pyridinyl)ethyl)-3,5-dimethyl-4-piperidinyl]propanamide | 119–120 | 0.205 | B |
| 24. | N-(phenyl)-N-[1-(2-(1H-pyrazol-1-yl)ethyl)-3,5-dimethyl-4-piperidinyl]propanamide | 169–170 | 0.209 | B |
| 25. | N-(phenyl)-N-[1-(2-(4-ethyl-4,5-dihydro-5-oxo-1H-tetrazol-1-yl)ethyl)-3,5-dimethyl-4-piperidinyl]propanamide | 77–79 | I | B |

*Inactive
**Major Isomer
***Minor Isomer

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A compound having the formula:

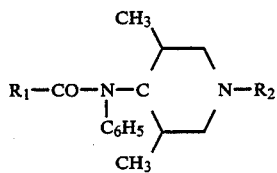

an optically active isomeric form thereof, a cis/trans isomeric form thereof or a pharmaceutically acceptable acid addition salt thereof, wherein:
  $R_1$ is selected from the group consisting of lower-alkyl, and lower-alkoxy lower-alkyl, each alkyl group having from 1 to 6 carbon atoms; and
  $R_2$ is pyrazoyl lower-alkyl.

2. The compound according to claim 1, wherein the $R_1$ group is a member selected from the group consisting of methyl, ethyl, methoxymethyl and 1-methoxyethyl.

3. The compound according to claim 1, wherein $R_2$ is 1H-pyrazol-1-yl lower-alkyl.

4. The compound according to claim 3, wherein $R_2$ is 2-(1H-pyrazol-1-yl)ethyl.

5. The compound according to claim 1, which comprises N-(phenyl)-N-[1-(2-(1H-pyrazol-1-yl)ethyl)-3,5-dimethyl-4-piperidinyl]methoxyacetamide, or the pharmaceutically acceptable addition salt thereof.

6. A narcotic analgesic composition comprising a non-toxic pharmaceutically acceptable carrier and an analgesically effective amount of a compound having the formula:

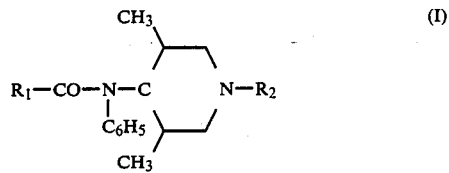

an optically active isomeric form thereof, a cis/trans isomeric form thereof or a pharmaceutically acceptable acid addition salt thereof, wherein:
  $R_1$ is selected from the group consisting of lower-alkyl, and lower-alkoxy lower-alkyl, each alkyl group having from 1 to 6 carbon atoms; and
  $R_2$ is pyrazolyl lower-alkyl.

7. The composition according to claim 6, wherein the $R_1$ group is a member selected from the group consisting of methyl, ethyl, methoxymethyl and 1-methoxyethyl.

8. The composition according to claim 6, wherein $R_2$ is 1H-pyrazol-1-yl lower-alkyl.

9. The composition according to claim 8, wherein $R_2$ is 2-(1H-pyrazol-1-yl)ethyl.

10. The composition according to claim 6, wherein the compound comprises N-(phenyl)-N-[1-(2-(1H-pyrazol-1yl)ethyl)3,5-dimethyl-4-piperidinyl]methoxyacetamide, or the pharmaceutically acceptable addition salt thereof.

11. A method of producing analgesia in a mammal, including respiratory depression, comprising administering to the mammal an analgesically effective amount of a compound having the formula:

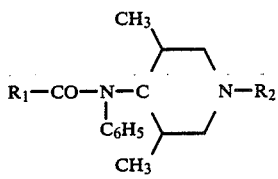

an optically active isomeric form thereof, a cis/trans isomeric form thereof or a pharmaceutically acceptable acid addition salt thereof, wherein:

$R_1$ is selected from the group consisting of lower-alkyl, and lower-alkoxy lower-alkyl, each alkyl group having from 1 to 6 carbon atoms; and $R_2$ is pyrazolyl lower-alkyl.

12. The method according to claim 11, wherein the $R_1$ group is a member selected from the group consisting of methyl, ethyl, methoxymethyl and 1-methoxyethyl.

13. The method according to claim 11, wherein $R_2$ is 1H-pyrazol-1-yl lower-alkyl.

14. The method according to claim 13, wherein $R_2$ is 2-(1H-pyrazol-1-yl)ethyl.

15. The method according to claim 11, wherein the compound comprises N-(phenyl)-N-[1-(2-(1H-pyrazol-1-yl)ethyl-3,5-dimethyl-4-piperidinyl]methoxyacetamide, or the pharmaceutically acceptable addition salt thereof.

* * * * *